United States Patent
Zeika et al.

(10) Patent No.: US 9,062,064 B2
(45) Date of Patent: Jun. 23, 2015

(54) HETEROCYCLIC COMPOUNDS AND THE USE THEREOF IN ELECTRONIC AND OPTOELECTRONIC COMPONENTS

(75) Inventors: Olaf Zeika, Theissen (DE); Horst Hartmann, Dresden (DE); Ulrich Heggemann, Dresden (DE); Sascha Dorok, Dresden (DE); Jan Blochwitz-Nimoth, Dresden (DE); Ansgar Werner, Dresden (DE); Michael Hofmann, Dresden (DE); Carsten Rothe, Dresden (DE)

(73) Assignee: NOVALED AG, Dresden (DE)

( * ) Notice: Subject to any disclaimer, the term of this patent is extended or adjusted under 35 U.S.C. 154(b) by 1037 days.

(21) Appl. No.: 13/139,658

(22) PCT Filed: Dec. 14, 2009

(86) PCT No.: PCT/DE2009/001744
§ 371 (c)(1),
(2), (4) Date: Sep. 6, 2011

(87) PCT Pub. No.: WO2010/075836
PCT Pub. Date: Jul. 8, 2010

(65) Prior Publication Data
US 2011/0309307 A1    Dec. 22, 2011

(30) Foreign Application Priority Data
Dec. 15, 2008    (DE) .......................... 10 2008 061 843

(51) Int. Cl.
| | |
|---|---|
| *H01B 1/00* | (2006.01) |
| *C07D 327/06* | (2006.01) |
| *C07D 497/04* | (2006.01) |
| *C07D 497/14* | (2006.01) |
| *C07D 497/22* | (2006.01) |
| *C09K 11/06* | (2006.01) |
| *H01L 51/00* | (2006.01) |
| *H05B 33/10* | (2006.01) |

(52) U.S. Cl.
CPC ................ *C07D 497/04* (2013.01); *H01B 1/00* (2013.01); *C07D 497/14* (2013.01); *C07D 497/22* (2013.01); *C09K 11/06* (2013.01); *C09K 2211/1011* (2013.01); *C09K 2211/1088* (2013.01); *C09K 2211/1096* (2013.01); *H01L 51/0071* (2013.01); *H05B 33/10* (2013.01); *Y02E 10/549* (2013.01)

(58) Field of Classification Search
None
See application file for complete search history.

(56) References Cited

U.S. PATENT DOCUMENTS

| | | |
|---|---|---|
| 4,769,292 A | 9/1988 | Tang et al. |
| 6,242,115 B1 | 6/2001 | Thomson et al. |
| 6,902,832 B2 | 6/2005 | Uchida et al. |
| 7,074,500 B2 | 7/2006 | Pfeiffer et al. |
| 7,274,141 B2 | 9/2007 | Leo et al. |
| 7,414,129 B2 | 8/2008 | Ehrenberg |
| 2003/0099865 A1 | 5/2003 | Uchida et al. |
| 2005/0110009 A1 | 5/2005 | Blochwitz-Nimoth et al. |
| 2005/0121667 A1 | 6/2005 | Kuehl et al. |
| 2005/0139810 A1 | 6/2005 | Kuehl et al. |
| 2005/0260451 A1 | 11/2005 | Kijima |
| 2006/0027834 A1 | 2/2006 | Forrest et al. |
| 2006/0033115 A1 | 2/2006 | Blochwitz et al. |
| 2006/0202196 A1 | 9/2006 | Kawakami et al. |
| 2006/0273310 A1 | 12/2006 | Birnstock et al. |
| 2006/0284170 A1 | 12/2006 | Leo et al. |
| 2007/0237982 A1 | 10/2007 | Inoue et al. |
| 2009/0045728 A1 | 2/2009 | Murano et al. |
| 2009/0217980 A1 | 9/2009 | Pfeiffer et al. |
| 2009/0235971 A1 | 9/2009 | Pfeiffer et al. |
| 2010/0102709 A1 | 4/2010 | Zeika et al. |
| 2010/0181555 A1* | 7/2010 | Hosokawa et al. ............. 257/40 |
| 2010/0289007 A1 | 11/2010 | Werner et al. |

FOREIGN PATENT DOCUMENTS

| | | |
|---|---|---|
| EP | 1478025 A2 | 11/2004 |
| EP | 1804308 A1 | 7/2007 |
| EP | 1804309 A1 | 7/2007 |
| GB | 2439030 A | 12/2007 |
| JP | 07-084386 | 3/1995 |
| JP | 63-296005 | 12/1998 |
| JP | 2004-101560 A | 2/2004 |
| JP | 2005314239 A | 11/2005 |
| JP | 2006135145 A | 5/2006 |
| WO | 2005/109542 A1 | 11/2005 |
| WO | 2006/092134 A1 | 9/2006 |
| WO | 2006/092135 A2 | 9/2007 |
| WO | 2007/106677 A2 | 9/2007 |
| WO | 2007/118799 A1 | 10/2007 |

OTHER PUBLICATIONS

Marti et al., "Synthesis, Properties, and X-ray Structure of 6-Aza-5,7,12,14-tetrathiapentacene as a Novel Polyheterocyclic Electron Donor, and Related Compounds," J. Org. Chem., 1994, 59 (21), pp. 6200-6207.
Chinese Office Action for Chinese Application No. 200980156831.5 mailed Apr. 2, 2013 (12 pages) (English translation).
English Translation of Office Action for JP Application No. 2011-539896 mailed Apr. 1, 2014.
Berges et al., "Organometallic Compounds with α-Phenylene Subsstituents, Part XV [1] Hexamethoxy-Tetrachalcogena-Tetrahydropentacene," Zeitschrift fuer Naturforschung, B, 1988, 43(5):599-604.

(Continued)

*Primary Examiner* — Harold Pyon
*Assistant Examiner* — Jaison Thomas
(74) *Attorney, Agent, or Firm* — Sutherland Asbill & Brennan LLP (57) ABSTRACT

The present invention relates to the use of heterocyclic compounds as the charge transport material, blocker material or light-scattering material in electronic, optoelectronic or electroluminescent components.

17 Claims, 2 Drawing Sheets

(56) References Cited

OTHER PUBLICATIONS

Boros et al., "Regiocontrolled Formation of a Novel Dioxadithiapentacene," Journal of Organic Chemistry, 1988, 63:10045-10047.

"[1,4]benzoxathiino[2,3-b]phenoxathiin," CA Index Guide or Ring Systems Handbook (published by the American Chemical Society), 1999.

Bard and Faulkner, Electrochemical Methods, Chapter 1: Introduction and Overview of Electrode Processes, 2nd Edition, 2000.

Berges, P. et al. "Elementorganische Verbindungen mit o-Phenylenresten, XV [1] Hexamethoxy-tetrachalcogena-tetrahydropentacene," Z. Naturforsch. 43b, 599-604 (1988).

Boros, E. "Regiocontrolled Formation of a Novel Dioxadithiapentacene," J. Org. Chem. 63, 1998, 10045-10047 (published by the American Chemical Society).

Boros, E. et al. "Preparation of Fluorinated Phenoxathiin Dioxide Monoamine Oxidase-A Inhibitors: Intramolecular Radical Substituion at Sulfur versus the Mauthner Synthesis," J. Heterocyclic Chem. 35, 1998, 699-706.

Connelly, Neil G. et al. "Chemical Redox Agents for Organometallic Chemistry," Chem. Rev. 1996, 96, 877-910.

D'Andrade, B. W. et al. "Relationship between the ionization and oxidation potentials of molecular organic semiconductors," Organic Electronics 6 (2005) 11-20.

Freund, T. et al. "Leiterpolymere mit Heteroacen-Gerust," Angew. Chem. 1994, 106, 2547.

Fu, Y. et al. "Quantum-chemical predictions of absolute standard redox potentials of diverses organic molecules and free radicals in acetonitrile," J. Am. Chem. Soc. 127, 2005, 7227-7234.

Goryunov, L. "Synthesis of Dimethylphosphorothiol Derivatives of Dibenzo-p-dioxin, Phenoxazine, and Phenoxathiyne," Russian J. of Organic Chemistry, vol. 4, No. 5, 2004.

Sato, N. et al. "Polarization Energies of Organic Solids Determined by Ultraviolet Photoelectron Spectroscopy," J. Chem. Soc., Faraday Trans. 2, 1981, 77, 1621-1633.

Sperotto, E. et al. "Ligand-free copper(I) catalyzed N- and O-arylation of aryl halides," Tetrahedron Letters 48 (2007) 7366-7370.

Walzer, K. et al. "Highly Efficient Organic Devices Based on Electrically Doped Transport Layers," Chem. Rev. 107, 2007, 1233-1271.

Zhang, J. et al. "The ground state spin multiplicity of Schlenk-type biradicals and the influence of additional linkage to ladder type structures," Chemical Physics 206, 1996, 339-351.

International Preliminary Report on Patentability for PCT Application No. PCT/DE2009/001744 mailed Jun. 21, 2011.

\* cited by examiner

HETEROCYCLIC COMPOUNDS AND THE USE THEREOF IN ELECTRONIC AND OPTOELECTRONIC COMPONENTS

CROSS-REFERENCE TO RELATED APPLICATIONS

This is a submission pursuant to 35 U.S.C. 154(d)(4) to enter the national stage under 35 U.S.C. 371 for PCT/DE2009/001744, filed Dec. 14, 2009. Priority is claimed under 35 U.S.C. 119(a) and 35 U.S.C. 365(b) to German Patent Application Number 10 2008 061843.8, filed Dec. 15, 2008. The subject matters of PCT/DE2009/001744 and German Patent Application Number 10 2008 061843.8 are hereby expressly incorporated herein by reference in their entirety.

TECHNICAL FIELD

The present invention relates to heterocylic compounds and their use as charge transport materials, light-scattering materials and/or blocking materials, preferably as hole conductors or electron blockers, in electronic, optoelectronic and electroluminescent components, such as organic light-emitting diodes (OLEDs), field effect transistors, photodetectors and organic solar cells (OPV).

BACKGROUND OF THE INVENTION

Organic light-emitting diodes (OLEDs) make use of the property of materials whereby they emitting light when suitable charge carriers are formed by applying a voltage. Recombination of these charge carriers forms excited states, which in turn enter the ground state by emitting light. OLEDs are an interesting alternative to cathode ray tubes and liquid crystal displays because they are suitable for production of flatscreen displays and displays for mobile applications, such as cellular phones, notebooks, PDAs, etc., due to their very compact design and their low power consumption.

To improve the efficiency of organic light-emitting diodes, they often have charge transport layers in addition to the actual emission layer, these transport layers being responsible for the transport of negative and positive charge carriers into the emission layer. These charge transport layers are divided into hole conductors and electron conductors, depending on the type of charge carriers transported.

Organic light-emitting diodes (OLEDs) usually consist of various layers of organic materials, at least one layer (emission layer) containing an electroluminescent substance which can be made to emit light by applying a voltage (Tang, U.S. Pat. No. 4,769,292). High-efficiency OLEDs are described in U.S. Pat. No. 7,074,500, for example.

Organic solar cells are known from the prior art, for example, US 2009217980 and US 2009235971. Organic solar cells comprise a layered stack on a substrate, such that the layered stack has at least one organic light-absorbing layer which is arranged between two electrodes (anode and cathode). At least one electrode must be transparent in the wavelength range in which the solar cell should function, typically in the strong absorption bands of the absorption layer in the visible and near-infrared ranges.

The absorption layer of a solar cell may be formed by a donor-acceptor heterojunction. This heterojunction may be a shallow junction, such that donors and acceptors are formed in adjacent layers (optionally with an intermediate layer). The heterojunction may also form a volume heterojunction such that donors and acceptors are mixed in the same layer.

Solar cells may also be stacked such that the at least two absorption layers are electrically linked by a pn-junction (also known as a recombination or connection unit). Such pn-junctions are known, for example, from US 2009045728 and EP 2045843.

Solar cells preferably also have organic hole and electron semiconductor layers which are essentially transparent. These are used for optical optimization, but they do not contribute toward the absorption. In addition all of these transport layers are preferably doped.

Doped OLEDs and doped solar cells as well as tandem solar cells are known from Walzer et al., Chem. Rev. 2007, 107, pages 1233-1271, for example.

Organic components are components containing at least one organic semiconductor layer. The organic semiconductor layers contain so-called "small molecules" among other organic molecules or also organic polymers, such that the organic molecules and the organic polymers either as a single layer or as a mixture with other organic materials (for example, described in US2005 0110009) or inorganic materials have semiconductor properties or metal-like properties.

As semiconductor components which constitute a high percentage of inorganic semiconductor elements and/or layers and at the same time contain one or more organic semiconductor layers or organic semiconductor materials or so-called organic-inorganic hybrid components. Within the context of the present invention, these hybrid components are also to be understood as organic components.

Components such as organic light-emitting diodes have a high potential for applications in the field of lighting and displays in particular in one embodiment for generating white light. In recent years, definite improvements have been achieved in this field with regard to the efficiency achieved as well as with regard to the lifetime of the components. The power efficiencies of stable white OLEDs today are in the range of 10 to 50 lm/W, and lifetimes of more than 10,000 hours can be implemented. For a broadly conceived commercialization in the field of general lighting applications, however, further improvements will be needed in particular with regard to the power efficiency because the market for highly efficient technologies for generating white light, for example, fluorescent tubes, is dominated today by efficiencies of up to 100 lm/W, for example.

Typical organic light-emitting diodes have the disadvantage that only approximately 25% of the light generated is emitted from the component. Approximately 50% of the light remains as internal modes in the arrangement of organic layers between the two electrodes. An additional 20% is lost in the substrate due to total reflection in the substrate. The reason for this is that the light is formed with a refractive index of approximately 1.6 to 1.8 within an OLED in optical media. If this light then strikes an optical medium with a lower refractive index, for example, another layer within an OLED stack, the substrate on which the OLED is formed or one of the electrodes, then complete reflection occurs if a certain value of the angle of incidence is exceeded.

For the use of white OLEDs in lighting technology it is also necessary to employ suitable output methods which can also be tied into the manufacturing process inexpensively. It is assumed today that an area of an OLED of 1 cm$^2$ for lighting applications may cost only a few cents if its application is to be economically reasonable. However, this also means that only especially inexpensive methods can be used at all to increase the light output. OLEDs based on so-called small molecules are processed today with the help of thermal evaporation in vacuo. OLEDs typically consist of two to twenty layers, all of which are vapor-deposited individually thermally. If it is possible now to significantly improve the output with the help of only a single additional thermally deposited layer, then at any rate the condition is fulfilled in the costs of the output method.

For applications of OLEDs as lighting elements, it is also necessary to design the components over a large area. For example, if an OLED is operated at a brightness of 1000 cd/m2, then areas in the range of several square meters would be necessary to illuminate an office room, for example.

According to the state of the art, benzidine derivatives such as N,N'-diphenyl-N,N'-bis(3-methylphenyl)-1,1'-biphenyl-4,4'-diamine (TPD), 4,4'-di-(N-carbazolyl)-diphenyl (CBP) and N,N'-di-(alpha-naphthyl)-N,N'-diphenyl-1,1'-biphenyl-4,4'-diamine (alpha-NPD) have been used in the past as hole-conducting materials and/or electron-blocking materials, but they lack thermal stability, which depends essentially on the glass transition temperature of these compounds (TPD: Tg=65° C.).

The lower thermal stability may result in destruction of the layered arrangement or mixing of different molecules from different layers, so that over time under thermal stress, an electronic or optoelectronic component will lose its efficiency.

Materials with polycyclic aromatic structures, for example, anthracene, pentacene, tetracene, phthalocyanines and also materials such as the fullerene C60 are used for components because of the high charge carrier mobility for organic materials. For example, thin-film field effect transistors (OTFT) may be mentioned here.

Through conventional methods such as vacuum vapor deposition, such components having multiple layers of an organic and/or polymer material can be produced. The relatively high crystallinity of the layers is partially also responsible for the high charge carrier mobility. However, layers of these molecules have the disadvantage of crystallization of the layer which can thus make the component unstable. Larger molecules, for example, sexithiophenes cannot be vaporized successfully without great decomposition.

The fullerenes, mainly C60 here, have a great n-charge carrier mobility and are also used as active semiconductor layers in OTFTs. However, C60 is very susceptible to contamination by oxygen, for example, and the components must be encapsulated at great expense.

In addition to the aforementioned organic materials there are hardly any organic materials which, at room temperature or higher temperatures, have a charge carrier mobility great enough to produce efficient OTFTs, for example, from them by the usual production methods. Other methods for efficient production of OTFTs are far less complicated and also require improvement (for example, change in the dielectrics of the surface, change in the dielectrics of the materials, charge carrier injection layers).

A high charge carrier mobility is desired to minimize the losses due to space charge effects in OLEDs or OPVs and also to increase the maximum usable frequency of digital or analog circuits as well as vibrating circuits (oscillators). New materials that exhibit a high conductivity with stable dopants are fundamentally desired.

A method of minimizing the power loss in organic components due to space charge effects is the use of doped layers. Doping increases the conductivity of the layer and thus bypasses the problem of the low charge carrier mobility.

It is known that organic semiconductors may be modified in their electrical properties, in particular in their electrical conductivity, by doping, as is the case with inorganic semiconductors (silicon semiconductors). By creating charge carriers in the matrix material, an increase in the initially quite low conductivity as well as a change in the Fermi level of the semiconductor are achieved, depending on the type of dopant used. Doping here leads to an increase in the conductivity of charge transport layers so that ohmic losses are reduced and an improved transition of the charge carriers between contact and organic layer is achieved. Doping is characterized by a charge transfer from the dopant to a nearby matrix molecule (n doping, electron conductivity increased) and/or by the transfer of an electron from a matrix molecule to a nearby dopant (p doping, hole conductivity increased). The charge transfer may be complete or incomplete and can be determined, for example, by the interpretation of the vibration bands from FT-IR measurements.

The conductivity of a thin-film sample can be measured using the so-called two-point method in which contacts made of a conductive material, for example, gold or indium-tin oxide, are applied to a substrate. Next, the thin film to be tested is applied to the substrate over a large area, so that the contacts are covered by the thin film. The current then flowing is measured after applying a voltage to the contacts. From the geometry of the contacts and the layer thickness of the sample, the conductivity of the thin-film material is obtained from the resistance thereby determined.

At the operating temperature of a component having a doped layer, the conductivity of the doped layer should exceed the conductivity of the undoped layer. To do so, the conductivity of the doped layer should be high at room temperature, in particular greater than $1\times10-8$ S/cm, but preferably in the range between 10-6 S/cm and 10-5 S/cm. Undoped layers have conductivities of less than $1\times10-8$ S/cm, usually less than $1\times10-10$ S/cm.

The thermal stability can be determined using the same method and/or the same structure by heating the layer (doped or undoped) in steps and measuring the conductivity after a resting time. The maximum temperature, which the layer can withstand without losing the desired semiconductor property, is then the temperature immediately before the conductivity collapses. For example, a doped layer on a substrate with two electrodes side by side as described above may be heated in increments of 1° C., waiting 10 seconds after each increment. Then the conductivity is measured. The conductivity changes with the temperature and drops abruptly above a certain temperature. The thermal stability therefore indicates the temperature up to which the conductivity does not collapse abruptly.

In these methods it is important to be sure that the matrix materials have a sufficiently high purity. Such purity can be achieved with traditional methods, preferably by gradient sublimation.

The properties of the various materials involved can be described through the energy layers of the lowest unoccupied molecular orbital (abbreviated: LUMO; synonym: electron affinity) and of the highest occupied molecular orbital (abbreviated: HOMO; synonym: ionization potential).

One method of determining ionization potentials (IP) is ultraviolet photoelectron spectroscopy (UPS). As a rule, ionization potentials are determined for the solid state but it is also possible to measure ionization potentials in the gas phase. The two values differ due to solid-state effects, for example, the polarization energy of the holes occurring in the photoionization process (N. Sato et al., J. Chem. Soc. Faraday Trans. 2, 77, 1621 (1981)). A typical value for the polarization energy is approximately 1 eV, but greater deviations may also occur.

The ionization potential is based on the start of the photoemission spectrum in the range of the high kinetic energies of the photoelectrons, i.e., the energies of the photoelectrons having the weakest bonding.

An associated method, namely inverted photoelectron spectroscopy (IPES) can be used to determine electron affinities (EA). This method is not very widespread however. Alternatively, solid-state energy levels may also be determined by electrochemical measurement of oxidation potentials (Eox) and reduction potentials (Ered) in solution. Cytovoltammetry (CV) is a suitable method. Empirical methods of deriving the solid-state ionization potential from an electrochemical oxidation potential are described in the literature (for example, B. W. Andrade et al., Org. Electron. 6, 11 (2005); J. Amer. Chem. Soc. 127, (2005), 7227.).

No empirical formulas are known for converting reduction potentials to electron affinities. This is due to the difficulty in determining electron affinities. Therefore a simple rule is often used: IP=4.8 eV+e·Eox (vs. ferrocene/ferrocenium) and/or EA=4.8 eV+e·Ered (vs. ferrocene/ferrocenium) (cf B. W. Andrade, Org. Electron. 6, 11 (2005) and refs. 25-28 therein). For the case when other reference electrodes or redox pairs are used for referencing the electrochemical potentials, conversion methods are known (cf. A. J. Bard, L. R. Faulkner, "Electrochemical Methods: Fundamentals and Applications," Wiley, 2nd edition, 2000). Information about influencing a solvent can be found in N. G. Connelly et al., Chem. Rev. 96, 877 (1996).

It is customary although not actually accurate to use the terms "energy of the HOMO" E(HOMO) and/or the "energy of the LUMO" E(LUMO) as synonymous with the terms ionization energy and/or electron affinity (Koopmans' theorem). It should be pointed out that the ionization potentials and electron affinities are such that a higher value means a stronger binding of a released or added electron. The energy scale of the molecular orbitals (HOMO, LUMO) runs in the opposite direction. Therefore in rough approximation it holds that: IP=−E(HOMO) and EA=−E(LUMO).

WO 2007/118799 describes quinoid heteroacene materials as organic semiconductors. JP 2002 124384 A2 describes 12-diazapentathanes and derivatives thereof. Diazapentathanes are also disclosed in US 2003 099865 A.

U.S. Pat. No. 6,242,115 B1 relates to organic light-emitting diodes in which asymmetrical charge transport materials having tertiary amine functions are used. These tertiary amine functions are constructed from the biphenyl core and two additional phenyl groups which are not joined together but may also be linked together directly or via a saturated or unsaturated bridge. A saturated and/or unsaturated C2 bridge is proposed as such a linkage but it must not have any additional substituents.

In the state of the art the lack of thermal stability, the charge carrier mobility and the atmospheric stability of the hole-conducting and/or electron-blocking compounds used so far in electronic, optoelectronic and electroluminescent components have represented a technical shortcoming which has limited the use of these components.

DETAILED DESCRIPTION OF EMBODIMENTS

Therefore one object of the present invention is to overcome the disadvantages of the state of the art and to provide materials which lead to improved electronic, optoelectronic and electroluminescent components, in particular hole-conducting, light-scattering and/or electron-blocking compounds. At the same time these compounds should also enable a higher efficiency of the components.

Another object of the invention is to provide materials having an oxidation potential between 0 V and 1.2 V (vs. ferrocene/ferrocenium); preferably between 0.2 V and 1.3 V (vs. ferrocene/ferrocenium); more preferably between 0.4 V and 1 V (vs. ferrocene/ferrocenium). A specific potential range for the oxidation potential is between 0.5 V and 0.8 V (vs. ferrocene/ferrocenium). These ranges are preferred to ensure an energetic adaptation to other layers of a component to transport holes into and out of other active organic transport layers, emitter layers of OLEDs and absorber layers in organic solar cells.

This object is achieved by using heterocyclic compounds according to Claim 1, the heterocyclic compounds as such, an organic semiconductor material, electronic, optoelectronic and electroluminescent components according to the independent claims. Preferred embodiments are derived from the subclaims.

It is especially preferred that the inventive heterocyclic compounds are used as a charge transport material, in particular as a hole transport layer and additionally or simultaneously as a (light) scattering layer in organic light-emitting diodes or solar cells.

An organic light-emitting component, in particular an organic light-emitting diode with an arrangement of stacked layers on a substrate is not inventive, where the arrangement of stacked layers has a base electrode which is optically transparent, a cover electrode, a layer arrangement which is formed which at least one organic light-emitting layer between the base electrode and the cover electrode and is in electrical contact therewith, and a light-scattering organic layer which is formed between the substrate and the base electrode and is in contact with the substrate and consists of a self-crystallizing organic material.

Within the context of the present invention, the term "dopant" is understood to be an electrical dopant which is also known as a redox dopant and has the properties described in the present invention.

The inventive heterocyclic compounds may be used successfully as a charge transport material, light-scattering material and/or blocking material in electronic, optoelectronic and electroluminescent components. They have an extremely high charge carrier mobility and a good stability in air. It should also be emphasized that the compounds can be manufactured very inexpensively. The required syntheses comprise rarely more than three synthetic transformations, usually even less. The yields of the reactions are good or very good. The starting materials used are usually inexpensively commercially available chemicals.

The heterocyclic compounds are those having the following formulas A-E:

where X and Y are different from one another but are otherwise selected independently from oxygen, sulfur, selenium and tellurium; n is 1, 2, 3, 4, 5 or 6; in formula A, R1-R6 are selected independently from alkyl, aryl, heteroaryl, anellated carbocycle, anellated heterocycle, OR', where R' is selected independently from aryl, heteroaryl, anellated carbocycle and anellated heterocycle, and NR2" as well as SR", where R" is selected independently from alkyl, aryl, heteroaryl, anellated carbocycle and anellated heterocycle; wherein for formula B, R1-R6 are selected independently from alkyl, aryl, heteroaryl, anellated carbocycle, anellated heterocycle, OR', SR' and NR2', where R' is selected independently from alkyl, aryl, heteroaryl, anellated carbocycle and anellated heterocycle; wherein for formulas C-E, R1-9 are selected from hydrogen, alkyl, aryl, heteroaryl, anellated carbocycle, anellated heterocycle, OR', SR' and NR2', where R' is selected independently from alkyl, aryl, heteroaryl, anellated carbocycle and anellated heterocycle.

If used, the term "alkyl" preferably denotes an alkyl group having up to 10 carbon atoms which may be arranged in a branched or linear manner.

Exemplary alkyl groups include methyl, ethyl, propyl, isopropyl, sec-butyl and isoamyl.

If used, the term "aryl" preferably denotes an aryl group with 6 to 20 carbon atoms, especially preferably phenyl, naphthyl, biphenyl or anthracenyl. The aryl group may also be substituted, for example, with one, two or three substituents. Substituents may preferably be selected from halogen, nitro, trihalomethyl, cyano, C1-4-alkyl, C1-4-alkoxy, C1-4-alkylthio, phenyl, benzyl, phenoxy or phenylthio.

If used, the term "heteroaryl" preferably denotes a carbocyclic aromatic ring system, preferably with a ring size of 5 to 8 atoms, which may have one or more, preferably 2 to 4 heteroatoms, selected from ONS or Se, for example. Examples of heteroaryl groups include pyridyl, furyl, imidazolyl, benzimidazolyl, pyrimidinyl, thienyl, quinolinyl, indolyl or thiazolyl. The heteroaryl group may optionally be substituted.

Anellated (aromatic) carbocycles include phenyl or naphthyl, for example.

Anellated (aromatic) heterocycles include, for example, pyridyl, furyl, imidazolyl, benzimidazolyl, pyrimidinyl, thienyl, quinolinyl, indolyl or thiazolyl.

The compounds described here and their derivatives are preferably used as hole transport materials (HTM) and/or as a scattering layer in electronic components. The electronic components may be organic solar cells, organic light-emitting diodes, organic thin-film transistors, diodes, photodiodes or others. The components may also be passive components, for example, current-conducting paths, current fuses, antennas and resistors. It is self-evident that the use of HTM in other semiconductor layers is possible and is not limited to the components described here.

It is especially preferable that the inventive heterocyclic compounds are used in at least one hole transport layer in solar cells, such that the at least one inventive hole transport layer is closer to the reflective electrode than to the transparent electrode.

Doped HTM layers may be used in various components, where there is a great flexibility in the choice of materials as soon as the desired conductivity is achieved. For special layers but usually not only in undoped layers, special energy levels are also required as in injection order extraction of charge carriers in intrinsic photoactive layers. In optoelectronic components the layers which serve for charge carrier transport must be essentially not light-absorbent.

The compounds described here and their derivatives may be used individually as a material layer or as a mixture with other materials which add functional properties to the layer, for example, mixtures with other HTM.

The novel materials are preferably doped with a p-dopant. Preferred p-dopants are known from U.S. Ser. No. 10/792133, U.S. 61/107,826 and U.S. Ser. No. 11/047972, for example. The dopant may be of an organic or inorganic type. The dopant may also be formed from a precursor. The dopants are preferably organic acceptors they then have an easier processability and a higher stability, especially a higher thermal stability against diffusion. Dopants with a molecular weight between 100 g/mol and 2000 g/mol, more preferably between 200 g/mol and 1000 g/mol, more preferably between 300 g/mol and 1000 g/mol are preferred. Molar doping concentrations are between 1:1000 (acceptor molecule:matrix molecule) and 1:2, preferably between 1:100 and 1:5, more preferably between 1:100 and 1:10. In individual cases, a doping ratio in which the doping molecule is used in a concentration higher than 1:2, for example, when an especially high conductivity is required may also be considered. An especially high conductivity is used when an organic electrode is produced as described in PCT/EP07/00208, for example.

The inventive materials and their derivatives are preferably used in OLEDs and hole transport layers (HTL) as a doped layer. It is also provided that an undoped layer may be used as an intermediate layer. The inventive materials, in particular the dioxa-dithia-pentacene derivates are also preferably used as electron blockers or as exciton blockers or both exciton blockers and electron blockers at the same time.

The inventive materials, in particular the dioxa-dithia-pentacene derivatives are preferably used in organic solar cells, in doped hole transport layers. The organic solar cells may also have an undoped layer as electron blockers, hole blockers or exciton blockers. Those skilled in the art are familiar with the structure of organic solar cells; see EP1861886 and EP1859494.

The inventive materials may also be used as part of a pn-junction if expedient. In particular a layer sequence . . . /light-emitting layer/ . . . /n-doped ETL/p-doped layer containing the inventive materials/ . . . /cathode (for OLED) and/or . . . /absorbent layer/ . . . /n-doped ETL/p-doped layer containing the inventive materials/ . . . /anode (for OPV). Optionally at least one intermediate layer may also be provided between the n-doped ETL and the p-doped layer containing the inventive materials.

It is also especially preferable that the heterocyclic compound is present in crystallized form in an organic light-scattering layer, preferably a compound of formulas A or B, where R1-6=H, or mixtures of the isomers of same are selected.

Compounds according to formulas D and E have a lower crystallinity. These materials are therefore especially suitable for producing stable components.

Compounds according to formulas A, B and C, mainly compounds according to formulas A and B have a higher crystallinity. It is to be expected that components with these compounds are less stable. It has surprisingly been found that the inventive layers already form crystalline layers without requiring any additional treatment (for example, thermal treatment). These crystalline layers are therefore stable.

Because of the high charge carrier mobility, the materials are preferably also used as the active layer in organic thin-film transistors. The active layer may also contain doped regions, for example, injection layers but is essentially undoped. Those skilled in the art are familiar with organic thin-film transistors and their production; see, for example, US2006202196.

It is also preferable that the inventive materials and their derivatives have a low absorption in the visible wavelength range, which is usually the case with the large HOMO-LUMO gap (band gap). A band gap of at least 1 eV is suitable, a band gap of at least 1.5 eV is preferred, a band gap of 2 eV is even more preferred. Doped or undoped transparent semiconductor layers are used in non-optically-active layers in optoelectronic components because the absorption in these layers reduces their efficiency. Doped or undoped transparent semiconductor layers are also used in completely or essentially transparent components to produce so-called transparent electronics. Transparent OLEDs are described, for example, in US20060033115 and in US20060284170.

According to the invention in an especially preferred embodiment an electronic, optoelectronic or electroluminescent component is provided which is bottom-emitting. This component has a layer arrangement based on a substrate comprising a base electrode arranged on the substrate and a cover electrode, through which base electrode light is emitted as well as at least one organic light-emitting layer arranged between the base electrode and the cover electrode. With the inventive structure of such a component, an improved output of light is obtained, such that the component can be produced inexpensively and is suitable for a mass production process. With the preferred inventive structure of the component, the electrode arranged closer to the substrate is referred to as the base electrode.

It is especially preferable that the light-scattering organic layer is formed from a single material in a single molecular structure.

It is also preferred that all the organic layers in the arrangement of stacked layers are fanned by thermal vaporization in vacuum by vaporizing organic material. For example, the VTE method (vacuum thermal evaporation) or sputtering methods are suitable methods.

It is also preferable that the material of the light-scattering organic layer is formed from a self-crystallizing organic material. It is preferable that the light-scattering organic layer comprises an organic material, which has a crystallization temperature in a range of less than approximately 60° C. In this way the organic material can crystallize itself in vapor deposition on the substrate without another heating step because the substrate temperature is usually between 20 and 60° C. in traditional VTE systems.

In another preferred embodiment, the light-scattering organic layer comprises an organic material which has a crystallization temperature in the range of less than approximately 200° C. In this way the organic material can be made to crystallize with the help of a heating step.

Furthermore, it is preferable that the light-scattering organic layer comprises a material which has a glass transition temperature of at least approximately 85° C. The lower limit of 85° C. is obtained from the fact that the finished component ultimately should have a thermal stability up to approximately 60° C. to 85° C.

The light-scattering organic layer preferably has a thickness of between 10 nm and 100 μm. Layer thicknesses between 100 nm and 100 μm are especially preferred. In the individual case, however, scattering component structures can be produced even with smaller layer thicknesses of less than 100 nm. In this case the surface roughness of the light-scattering organic layer imposes a surface roughness onto these following layers. If a light-scattering organic layer has an interface formed by two materials with a different refractive index and/or with a different dielectric constant, then there is scattering of light on this refractive index gradient. Such an interface may be formed, for example, by an organic layer and a (following) metallic layer. Suitable metals include in particular aluminum, silver, magnesium, barium, calcium and molybdenum. It is surprising here that even small nominal layer thicknesses, for example, 10 nm to 50 nm may produce a substantial surface roughness. This is attributed to the special growth behavior, in particular the tendency to form crystalline structures of the materials. It is especially advantageous that the cover electrode forms a whitish appearance. Light of any wavelength is evidently scattered well by the electrode. The base electrode may be a TCO (transparent conducting oxide), preferably an ITO (indium-tin oxide) which can be applied by sputtering. The cover electrode may preferably be a light-reflective electrode, for example, a metal electrode. In one embodiment, the substrate is glass. In another embodiment, the substrate has an optical refractive index in a range of approximately 1.4 to 1.8.

It is often expedient if one or more layers are formed on the base electrode before the light-scattering organic layer is formed. In this way the formation of short circuits between the base electrode and the cover electrode is effectively suppressed. The one or more layers on the base electrode preferably have a low surface roughness of <5 nm RMS and/or are preferably formed from amorphous materials. In particular it is expedient to form the light-scattering organic layer on the side of the function layer of the component facing away from the base electrode. This function layer is, for example, a light-absorbing layer or a light-emitting layer.

Due to the use of the light-scattering organic layer, not only is the light output improved but also the angle dependence of the light emission is improved. To do so one must know that a white light spectrum contains components of several colors, but typically at least blue, green and red light. Since the emission characteristics for various wavelengths are different, different colors are observed at different angles of viewing. This is drastically reduced by the scattering properties of the organic layer.

A factor to be taken into account here is that the grain boundaries of the crystallites on which the scattering occurs are large enough.

Therefore the crystallites of the light-scattering organic layer should on the average preferably be larger than 500 nm.

Those skilled in the art are familiar with the typical structure of the standard OLED, which may be as follows:
1. carrier, substrate, for example glass,
2. electrode, hole-injecting (anode=positive pole), preferably transparent, for example, indium-tin oxide (ITO),
3. hole injection layer, for example, CuPc (copper phthalocyanine) or starburst derivates,
4. hole transport layer, for example, TPD (triphenyl-diamine and derivates),
5. blocking layer on the hole side to prevent exciton diffusion out of the emission layer and to prevent charge carrier leakage out of the emission layer, for example, alpha-NPB (bis-naphthyl-phenylamino-biphenyl),
6. light-emitting layer or system of multiple layers contributing to light emission, for example, CBP (carbazole derivatives) with added emitter (for example, phosphorescent triplet emitter iridium tris-phenylpyridine Ir(ppy)3) or Alq3 (tris-quinolinato-aluminum) mixed with emitter molecules (for example, fluorescent singlet emitter coumarin),
7. blocking layer on the electron side to prevent exciton diffusion out of the emission layer and to prevent charge carrier leakage out of the emission layer, for example, BCP (bathocuproines),
8. electron transport layer, for example, Alq3 (tris-quinolinato-aluminum),
9. electron injection layer, for example, inorganic lithium fluoride (LiF),
10. electrodes, usually a metal with a lower work function, electron-injecting (cathode=negative pole), for example, aluminum.

Layers may of course be omitted or a layer (or a material) may assume multiple properties, for example, layers 3 and 4, 4 and 5, 3-5 may be combined and/or layers 7 and 8, 8 and 9, and 7-9 may be combined. Additional possibilities provide for mixing the substance from layer 9 into layer 8, etc.

A reflective electrode and organic layers are normally deposited on a substrate by vacuum vapor deposition. The electrode may also be sputtered. The organic layers may also be prepared from solvents, for example, by spin coating and inkjet printing.

This structure describes the non-inverted (anode on the substrate), substrate-emitting (bottom-emission) structure of an OLED. There are various concepts for describing OLEDs that emit away from the substrate (see references in DE 102 15 210.1), but all these concepts have in common the fact that then the electrode on the substrate side (the anode in the non-inverted case) is reflective (or transparent for a transparent OLED) and the cover electrode is designed to be (semi-)transparent. This is usually associated with losses in terms of the power parameters.

If the sequence of the layers is inverted (cathode on substrate), we speak of inverted OLEDs (see references in DE 101 35 513.0). Here again, power losses may be expected in the absence of special measures.

The organic layer arrangement of an OLED or a solar cell typically comprises multiple organic layers arranged one above the other. Within the organic layer arrangement, one or more pn-junctions may be provided as is known for stacked OLEDs (cf. EP 1 478 025 A2), where such a pn-junction is formed in one embodiment with the help of p-doped hole transport layer and an n-doped electron transport layer which are formed in direct contact with one another. Such a pn-junction is an electrical charge-producing structure in which electrical charges are generated preferably in the borderline area between the two layers when an electrical potential is applied.

In solar cells and photosensors, the pn-junction is also used to connect stacked heterojunctions and thus to add the voltage generated by this component (US2006027834A). The junctions have the same function as tunnel junctions in stacked inorganic heterojunction solar cells, although the physical mechanisms are presumably not the same.

The junctions are also used to obtain improved injection (extraction in the case of solar cells) to the electrodes (EP 1808910).

To improve the energetic properties in an organic electronic component, proposed in the document WO 2005/109542 A1 that a pn-junction be formed with a layer of an organic semiconductor material of the n-type and a layer of an organic material of the p-type such that the layer of the organic semiconductor material of the n-type is in contact with an electrode embodied as an anode. In this way, an improved injection of charge carriers in the form of holes into the layer of the organic semiconductor material of the p-type is achieved.

To stabilize the pn-junction, a layer of another material is used as an intermediate layer. Such stabilized pn-junctions are described, for example, in US2006040132A, where a metal is used as the intermediate layer. OLEDs having this metal layer have a shorter lifetime because of the diffusion of the metal atoms.

With the inventive materials, stable intermediate layers and/or doped intermediate layers may be provided between the pn-junctions to produce stable organic semiconductor components.

It is known that such a pn-junction functions very efficiently when both materials of the pn-type and the n-type are doped (EP1804308, EP1804309).

It is also possible to produce a material and a material combination to provide an efficient and stable, mainly thermal stable pn-junction.

In OLEDs, pn-junctions are also known as charge generation layers or connection units. In solar cells, pn-junctions are also known as recombination layers.

Additional features and advantages of the invention are derived from the following detailed description of exemplary embodiments taking into account the accompanying drawings, in which.

COMPARATIVE EXAMPLE 1

Solar Cell According to the State of the Art

A solar cell (essentially according to FIG. 2) was produced on a glass substrate with the following layer structure:
ITO anode with a layer thickness of 90 nm;
zinc phthalocyanine: C60 D-A-volume heterojunction (concentration 1:2) with a layer thickness of 40 nm;
4,4'-bis[N-(1-naphthyl)-N-phenyl-amino]-biphenyl as a hole transport layer (HTL), doped with 2,2'-(perfluoronaphthalene-2,6-diylidene)dimalononitrile (3 mol %), with a layer thickness of 70 nm;
5 nm zinc phthalocyanine, doped with 2,2'-(perfluoronaphthalene-2,6-diylidene)-dimalononitrile (3 mol %) as a contact-improving layer;
60 nm Au as the cathode.

EXAMPLE 2

Solar Cell According to the Invention

A solar cell having the following layer structure (essentially according to FIG. 8) was produced on a glass substrate:
ITO anode with a layer thickness of 90 nm;
zinc phthalocyanine: C60 D-A-volume heterojunction (concentration 1:2) with a layer thickness of 40 nm;
4,4'-bis[N-(1-naphthyl)-N-phenyl-amino]-biphenyl as a hole transport layer (HTL), doped with 2,2'-(perfluoronaphthalene-2,6-diylidene)dimalononitrile (3 mol %), with a layer thickness of 10 nm;
dithiadioxapentacene as a hole transport layer and scattering layer doped with 2,2'(perfluoronaphthalene-2,6-diylidene)dimalononitrile (3 mol %), with a layer thickness of 60 nm;
5 nm zinc phthalocyanine, doped with 2,2'-(perfluoronaphthalene-2,6-diylidene)-dimalononitrile (3 mol %) as a contact-improving layer;
60 nm Au as the cathode.

The two solar cells were not optimized with regard to their layer thicknesses. Significant improvements were in the photovoltaic properties of the inventive solar cell. The solar cell according to the inventive Example 2 had a 49% (relatively) greater FF (fill factor), a 78.5% higher short-circuit current and a better saturation in comparison with the reference solar cell from Comparative Example 1.

A measurement under diffuse insolent light showed that the solar cell according to Example 2 has a much better efficiency. An investigation by simulation has shown that the layer thicknesses of the solar cell from Comparative Example 1 are optimized for white light with perpendicular incidence. In contrast with that, the solar cell from Example 2 has a low cavity due to the scattering layer and has a good performance even without perpendicular incidence.

Example 2 was repeated with a compound A or B, where R1-6=H and n=2, and here again, this solar cell had better results than the solar cell from Comparative Example 1.

COMPARATIVE EXAMPLE 3

OLED with a Thick HTL

OLEDs were produced having the following layer structure on a glass substrate:
90 nm ITO as cathode;
30 nm 2,4,7,9-tetraphenyl-1,10-phenanthroline as the electron transport layer doped with tetrakis(1,3,4,6,7,8-hexahydro-2H-pyrimido[1,2-a]pyrimidinato)ditungsten (II), 1 mol %;
10 nm 2,4,7,9-tetraphenyl-1,10-phenanthroline as the undoped intermediate layer;
20 nm red emitter layer: 20-nm-thick rubrene emitter layer doped with a commercial red dye (10 wt %). DCJTB (4-(dicyanomethylene)-2-tert-butyl-6-(1,1,7,7-tetramethyl-julolidyl-9-enyl)-4H-pyran) may also be used as a red emitter dopant;
10 nm 4,4'-bis[N-(1-naphthyl)-N-phenyl-amino]-biphenyl as an EBL;

X nm 4,4'-bis[N-(1-naphthyl)-N-phenyl-amino]biphenyl, doped with 2 mol % 2,2'-(perfluoronaphthalene-2,6-diylidene)dimalononitrile as a hole transport layer;
200 nm aluminum as the anode;
where X=40, 100, 150, 200, 300, 400, 500 and 800 nm.

EXAMPLE 4

OLEDs with a Scattering Layer, in which One Layer is Simultaneously the HTL and Scattering Layer Eight OLEDs were produced according to Example 3 (essentially according to FIG. 6), where the HTL was replaced by a dithiadioxapentacene layer doped with 2 mol % 2,2'-(perfluoronaphthalene-2,6-diylidene)dimalononitrile.
Eight different layer thicknesses of the HTL were investigated, and it was found that the OLEDs with dithiadioxapentacene and with layer thicknesses equal to or greater than 100 nm had a higher efficiency than the comparative example.

EXAMPLE 5

Example 4 was repeated with a compound A or B, where R1-6=H and n=2. Here again an improvement was found in comparison with the comparative example.

EXAMPLE 6

Example 4 and Comparative Example 3 were repeated in a top-emitting design (essentially according to FIG. 3), where X=150 nm and the cathode consisted of 100 nm Ag and the anode consisted of 100 nm ITO.
The OLEDs with doped dithiadioxapentacene as the HTL had a higher efficiency than in the comparative examples.

COMPARATIVE EXAMPLE 7

White-Emitting OLED

OLEDs were produced with the following layer structure on a glass substrate:
100 nm Ag as cathode;
n-doped electron transport layer: 30 nm BPhen doped with Cs;
intermediate layer on the electron side: 10 nm bathophenanthroline (BPhen);
blue emission layer: 20 nm 4,4'-bis[N-(1-naphthyl)-N-phenyl-amino]-biphenyl;
orange-red emission layer: 10 nm 4,4'-bis[N-(1-naphthyl)-N-phenyl-amino]-biphenyl doped with iridium(III)bis(2-methyldibenzo[f,h]quinoxaline)(acetylacetonate) (RE076, ADS);
intermediate layer on the hole side: 10 nm N,N'-bis(3-methylphenyl)-N,N'-bis-(phenyl)-benzidine (TPD);
p-doped hole transport layer: 150 nm 4,4',4''-tris(N,N-diphenylamino)triphenylamine (Starburst TDATA), doped with tetrafluoro-tetracyano-quinodimethane (F4-TCNQ);
20 nm Ag as the anode;
80 nm ITO to increase the conductivity of the anode.
A strong cavity effect was manifested in the comparative example due to the high angular dependence of the emitted color.

EXAMPLE 8

White-Emitting OLED

Figure 3:
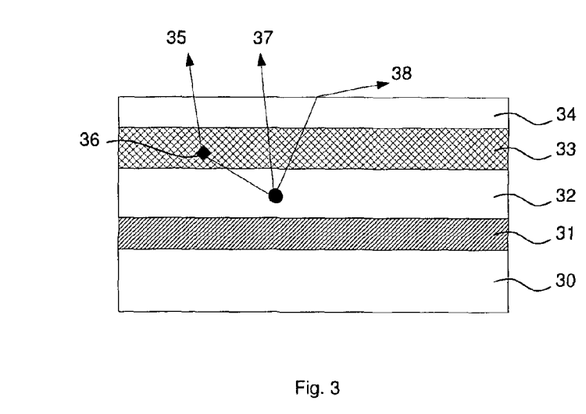
FIG. 3 shows schematically a cross section through a top-emitting OLED in a non-inverted embodiment.

The OLED according to Example 7 was produced but using p-doped dithiadioxapentacene as the HTL (essentially according to FIG. 3). In the OLED with dithiadioxapentacene, the efficiency was higher and the angle dependenceced was greatly reduced.

EXAMPLE 9

Top-Emitting OLED with a Scattering Layer

Figure 7:
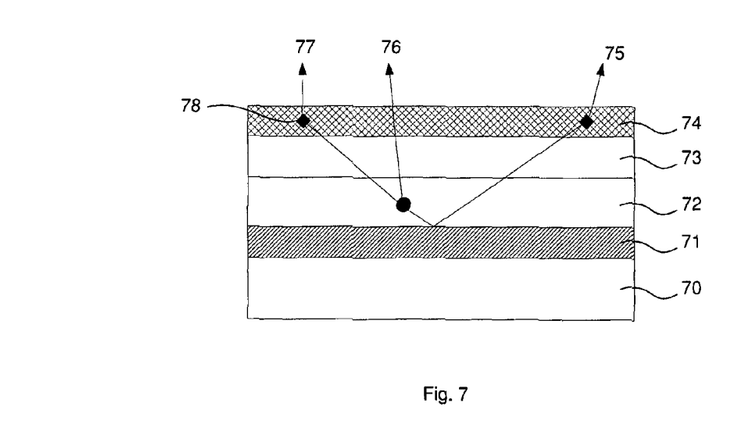
FIG. 7 shows schematically a cross section through a top-emitting OLED with an emitter layer.

Top-emitting OLEDs were produced with the following layer structure on a glass substrate, essentially according to FIG. 7.
100 nm Ag as the cathode;
4,4'-bis[N-(1-naphthyl)-N-phenyl-amino]-biphenyl as the hole transport layer (HTL), doped with 2,2'-(perfluoronaphthalene-2,6-diylidene)dimalononitrile (3 mol %);
4,4'-bis[N-(1-naphthyl)-N-phenyl-amino]-biphenyl with a layer thickness of 10 nm;
5-nm-thick layer of 4,4'-bis[N-(1-naphthyl)-N-phenyl-amino]-biphenyl 3 mol %, doped with a yellow emitter (YD3 from Eastman Kodak);
25 nm blue emitter layer BH121, doped with 5 mol % EK9 (both from Eastman Kodak);
10 nm 4-(naphthalen-1-yl)-2,7,9-triphenylpyrido[3,2-h]quinazoline;
4-(naphthalen-1-yl)-2,7,9-triphenylpyrido[3,2-h]quinazoline doped with 4,4',5,5'-tetrakis(3,5-dimethylcyclohexyl)-1,1',2,2',3,3'-hexamethyl-2,2',3,3'-tetrahydro-1H,1'H-2,2'-bisimidazole (10 mol %) as ETL;
18 nm Ag as the cathode;
80 nm ITO to increase the conductivity of the anode.
1035-nm-thick cover layer.

Figure 1:
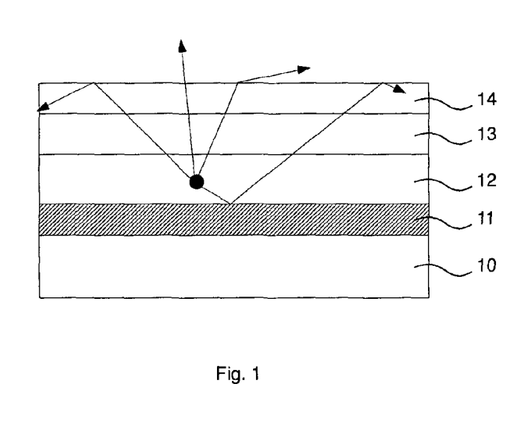
FIG. 1 shows schematically a cross section through an OLED according to the state of the art.

| Sample | d HTL (nm) | d ETL (nm) | Cover layer | $P_{\text{eff}}$ (lm/W) | EQE (%) | $\Delta_{CC}$ |
|---|---|---|---|---|---|---|
| 9A | 30 | 95 | 4,4'-bis[N-(1-naphthyl)-N-phenyl-amino]-biphenyl | 6.50 | 3.14 | >0.1 |
| 9B | 30 | 95 | 5,12-dioxa-7,14-dithia-pentacene | 15.9 | 6.32 | <0.02 |
| 9C | 185 | 95 | 4,4'-bis[N-(1-naphthyl)-N-phenyl-amino]-biphenyl | 11.84 | 4.63 | >0.1 |
| 9D | 185 | 95 | 5,12-dioxa-7,14-dithia-pentacene | 8.12 | 2.96 | <0.02 |
| 9E | 185 | 20 | 4,4'-bis[N-(1-naphthyl)-N-phenyl-amino]-biphenyl | 11.44 | 4.52 | ~0.2 |
| 9F | 185 | 20 | 5,12-dioxa-7,14-dithia-pentacene | 8.49 | 2.44 | ~0.03 |

Where d HTL is the layer thickness in nm, Peff (lm/W) is the efficiency at 1000 nits, EQE is the external quantum efficiency at 1000 nits, and ΔCC is the angle deviation from the color coordinates d (color coordinates) measured in an angular range from 0° (perpendicular to the surface) to 80°. The layer thicknesses used are optimized values.
Example 9 was also repeated successfully with compounds A or B, where R1-6=H and n=2.
FIG. 1 shows an OLED according to the state of the art. A top-emitting OLED was used in the example but the result can also be applied to a bottom-emitting OLED. The OLED contains a substrate on which the organic semiconducting layers are applied between two electrodes. The structure shown has a reflective anode 11 on the substrate 10, an emitter layer 12 on the cathode 11, a hole transport layer (HTL) 13 on the emitter layer 12 and a transparent anode 14. However, this structure could also be non-inverted (anode on the substrate).

FIG. 1 shows that not all the light generated is emitted to the outside. The production of light is represented by the black circular area. The light which is produced at a shallow angle (in relation to the substrate) is passed through internal modes and possibly absorbed. Thus only approximately ¼ of the light produced can be emitted from the component.

Figure 2:
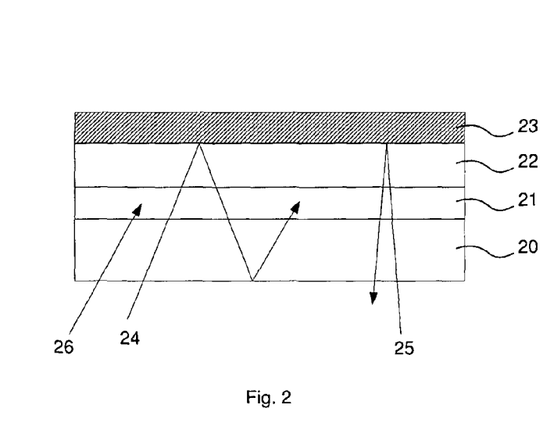
FIG. 2 shows schematically a cross section through an organic solar cell according to the state of the art.

FIG. 2 shows an organic solar cell according to the state of the art. The structure typically includes a transparent electrode 21, a reflecting electrode 23 and at least one organic semiconductor layer 22 which absorbs the light, and this organic semiconductor layer 22 is situated between the electrodes. This structure is applied as usual to a transparent substrate 20, but other variants such as a transparent cover electrode and a not necessarily transparent substrate are also possible.

In the solar cell according to FIG. 2, light is transferred through the substrate 20 and through the base electrode 21. The light is eventually absorbed by the organic layers (beam of light 26). If the light is not absorbed, it is reflected. If the incident light has shallow angle, as illustrated with the beam of light 24, it may be reflected by internal total reflection in the component until it is absorbed. If the incident light has a high angle, as illustrated with beam of light 25, the light may not be absorbed and may be output again, so losses occur.

FIG. 3 shows a top-emitting OLED in the inverted design (cathode on the substrate). A reflecting cathode 31 is formed on a substrate 30. Emitter layer 32 and HTL 33 are formed between the anode 31 and the transparent cathode 34. The HTL 33 has the property of scattering light.

FIG. 3 shows how a beam of light 35 which is emitted at a shallow angle, scattered through the HTL layer 3 and is thus output. The scattering elements (36) are intrinsic with the layer 33. Beam of light 37 and beam of light 38 may be output with or without scattering. The additional light increases the efficiency of the OLED.

Figure 4:
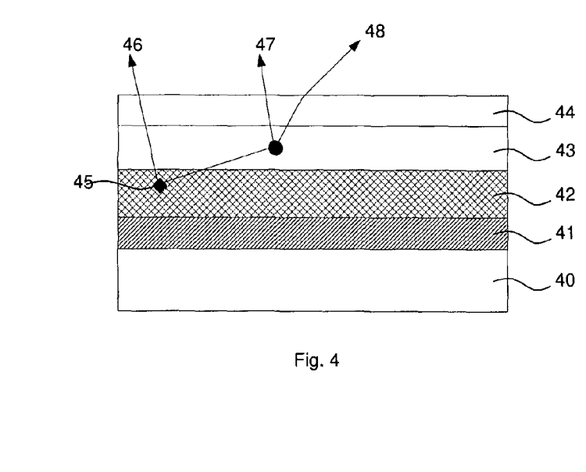
FIG. 4 shows schematically a cross section through a top-emitting OLED in an inverted embodiment.

FIG. 4 shows a top-emitting OLED in the non-inverted embodiment (anode on the substrate). A reflective anode 41 is formed on a substrate 40. Emitter layer 43 and HTL 42 are formed between the anode 41 and the transparent anode 44. HTL 42 the property of scattering light.

FIG. 4 shows how a beam of light 46 which is emitted at a shallow angle is scattered by the HTL layer 42 and is thus output. The scattering elements 45 are intrinsic with the layer 42. Beam of light 47 and beam of light 48 may be output with or without scattering. The additional light increases the efficiency of the OLED.

The embodiment of FIG. 4 is preferred over the embodiment of FIG. 3 because in the top-emitting OLED with an inverted structure, the direct light (47, 48) is not scattered as in FIG. 3 (37, 38). Nevertheless, both embodiments have the additional advantage that the color angle dependence of the emitted light is reduced.

Figure 5:
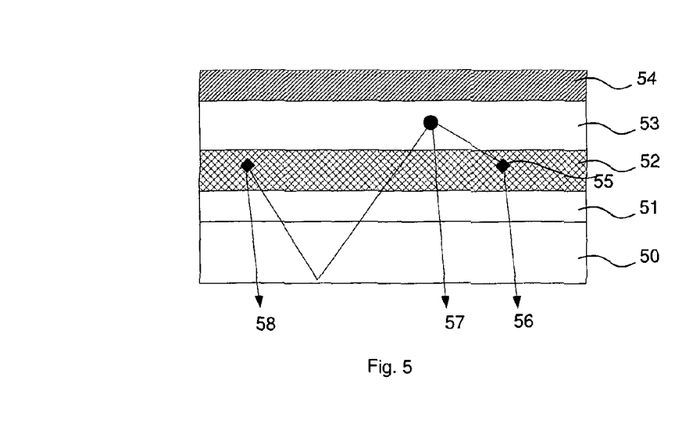
FIG. 5 shows schematically a cross section through a bottom-emitting OLED in a non-inverted embodiment.

FIG. 5 shows a bottom-emitting OLED in the non-inverted embodiment (anode on the substrate). A transparent anode is formed on a transparent substrate 50. Emitter layer 53 and HTL 52 are formed between the transparent anode 51 and the reflective cathode 54. The HTL 52 has the property of scattering light.

FIG. 5 shows how beam of light 58 and beam of light 56, which are emitted at a shallow angle, are scattered by the HTL layer 52 and are thus output. The scattering elements 55 are intrinsic with the layer 52. Beam of light 57 may be output with or without scattering. The additional light increases the efficiency of the OLED.

Figure 6:
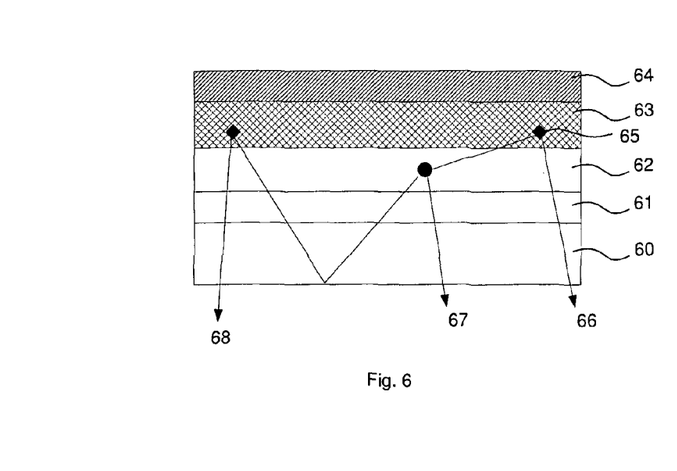
FIG. 6 shows schematically a cross section through a bottom-emitting OLED in an inverted embodiment.

FIG. 6 shows a bottom-emitting OLED in the inverted embodiment (cathode on the substrate). A transparent cathode 61 is formed on the transparent substrate 60. Emitter layer 62 and HTL 63 are formed between the transparent cathode 61 and the reflective anode 64. The HTL 63 has the property of scattering light.

FIG. 6 shows how beam of light 68 and beam of light 66 which are emitted at a shallow angle are scattered by the HTL layer 63 and are thus output. The scattering elements (65) are intrinsic in the layer 63. Beam of light 67 may be output without scattering. The additional light increases the efficiency of the OLED.

The embodiment of FIG. 6 is preferred over the embodiment of FIG. 5, because in the bottom-emitting OLED with the inverted structure, the direct light 67 is not scattered as in FIG. 5 (57). However, both embodiments have the additional advantage that the color-angle dependence of the emitted light is reduced.

FIG. 7 shows a top-emitting OLED with an emitter layer 72 between a reflective base electrode 71 and a transparent cover electrode 73 on a substrate 70. The OLED includes a scattering layer 74 on the cover electrode 73 (not between the electrodes).

FIG. 7 shows how beam of light 77 and beam of light 75, which are emitted at a shallow angle, are scattered by the scattering layer 74 and are thus output. The scattering elements (78) are intrinsic in the layer 74. Beam of light 76 may be output without scattering. The additional light increases the efficiency of the OLED.

Figure 8:
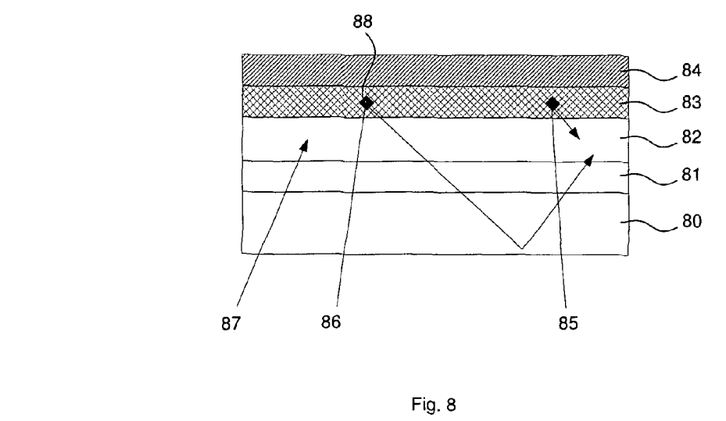
FIG. 8 shows schematically a cross section through an organic solar cell with a hole transport layer which at the same time is a scattering layer.

FIG. 8 shows an organic solar cell with a hole transport layer 83, which is a scattering layer at the same time. The solar cell includes an organic absorption layer 82 (typically a heterojunction or volume heterojunction) and an HTL 83 between a transparent cathode 81 and a reflective anode 84 on a transparent substrate 80.

FIG. 8 shows how the incident beams of light 86, 85, which are not absorbed directly, are scattered by the HTL 83. The incident light 87 may be absorbed directly or may be reflected by the reflected anode 84. The HTL and the scattering layer increase the probability that light striking at a high angle will be converted into internal modes, which ultimately increases the probability of absorption and the efficiency.

The organic layer arrangement must include at least one light-emitting layer. Typical layer arrangements for OLEDs are described in EP1705727, EP1804309. The OLED may also have a p-i-n layer arrangement as described in U.S. Pat. No. 7,074,500, US2006250076. The n- and p-dopants which are used in a p-i-n OLED are described in U.S. Pat. No. 6,908,783, US2008265216, WO07107306, EP1672714, for example.

SYNTHESIS EXAMPLE 1

5,12-Dioxa-7,14-dithia-pentacene

Potassium t-butanolate (2.78 g; 24.8 mmol) was suspended in 30 mL anhydrous dimethylformamide under a protective gas atmosphere. The suspension was cooled to 0° C. and 2-mercaptophenol (1.96 g; 15.5 mmol) was added slowly by drops to 30 mL anhydrous dimethylformamide. After removing the ice bath, the reaction mixture was stirred for 30 minutes more until a viscous light yellow solution had formed. 1,2,4,5-Tetrafluorbenzene (0.93 g; 6.20 mmol) was added and the mixture was heated at reflux for two days. Next the dimethylformamide was removed in vacuo and the residue was dissolved in 30 mL chloroform. The organic phase was washed three times with 15 mL water and then dried with sodium sulfate. The solvent was removed in vacuo and the residue was recrystallized from chloroform/methanol and 1.10 g (50%; 3.4 mmol) was isolated as a white solid, melting point: 223° C.

SYNTHESIS EXAMPLE 2

5,9,16-Trioxa-7,14,18-trithiaheptacene

First Step: Synthesis of Tetrabromophenoxathiine 10 g phenoxathiine (49.9 mmol) was suspended in 250 mL trifluoroacetic acid and cautiously mixed with 23.0 mL bromine (71.7 g, 449 mmol, 9 eq.). The mixture was stirred for 3 days at room temperature and checked on the basis of GCMS (THF as the mobile phase). After the end of the reaction, the reddish-brown reaction mixture was mixed with saturated Na2SO3 solution until it had completely decolorized. The precipitated solids were filtered with suction and washed with Na2SO3 solution, water and finally methanol and then dried. The light-brownish solids were recrystallized from toluene, yielding 18.0 g product in the form of a pure white solid (GCMS 98% pure).

Second Step: Reaction of Tetrabromophenoxathiine 0.61 g 2-mercaptophenol (4.8 mmol, 2.5 eq.) was dissolved in 12 mL DMF under argon and added by drops to a suspension of 1.34 g potassium carbonate (9.7 mmol, 10 eq.) in 12 mL DMF. The mixture was stirred for 30 minutes and then 1.00 g tetrabromophenoxathiine (1.9 mmol) was added. The mixture was then heated at reflux for at least 4 days (reaction control by HPLC-MS C18). After the end of the reaction, the DMF was removed under a reduced pressure and the residue was dissolved in 100 mL chloroform and stirred with water, 1N sodium bicarbonate solution and again with water (50 mL each). The remaining undissolved solids were filtered out and the organic phase was dried and concentrated. The undissolved solids (4.2 g) were dissolved in two liters of toluene at reflux, filtered and concentrated to approximately 250 mL. The mother liquor yielded 3.0 g product in the form of pure white precipitated crystals (95% according to HPLC). The organic phase additionally yielded 1.0 g product as a yellow solid (approximately 95% according to HPLC), melting point: 268° C. by recrystallizing twice from toluene.

SYNTHESIS EXAMPLE 3

3,10-Dimethoxy-5,12-dioxa-7,14-dithiapentacene

First Step: Methylation of 6-hydroxy-1,3-benzoxanthiol-2-one (thioxolone)

6.50 g (38.7 mmol) 6-hydroxy-1,3-benzoxanthiol-2-one was dissolved in 130 mL DMF and mixed with 4.27 g (30.9 mmol, 0.8 eq.) potassium carbonate. To the reaction mixture was added 3.10 mL (7.09 g, 50.3 mmol, 1.3 eq.) methyl iodide cautiously by drops. The reaction was stirred overnight, poured onto ice water and then extracted with chloroform. The organic phase was dried over sodium sulfate and concentrated. The solid residue was dissolved in methanol, stirred and filtered. The dry pure white solids (GCMS purity 100%, M=182) were obtained in a yield of 4.60 g (65% of the theoretical).

Second Step: Splitting the Heterocycle 4.50 g (24.8 mmol) 6-methoxy-1,3-benzoxathiol-2-one was suspended in 56 mL methanol and mixed with 4.40 g (66.4 mmol) 85% potassium hydroxide, which had previously been dissolved in 11 mL methanol and 17 mL water. The suspension dissolved, forming a yellow color and was stirred for approximately 10 minutes (TLC control). After the end of the reaction the reaction mixture was cautiously acidified to a pH of 1 using 1N aqueous hydrochloric acid, the methanol was removed under a reduced pressure and the residue was extracted twice with ethyl acetate. The organic phases were combined and each was washed twice with water, saturated sodium chloride solution and again with water. After drying with sodium sulfate and removing the solvent under a reduced pressure, 3.55 g (92%) 5-methoxy-2-mercaptophenol was obtained as a light-yellowish fluid. The raw product (GCMS 100%, M=156) was used further without further purification.

Third Step: Reaction with 1,2,4,5-tetrafluorbenzene 0.72 g (6.40 mmol) dry potassium tert-butylate was suspended in 10 mL dry DMF. While cooling with ice, 0.50 g (3.2 mmol) 5-methoxy-2-mercaptophenol in 10 mL dry DMF was added cautiously to this suspension. The mixture was stirred for 30 minutes at RT and then mixed with 0.14 mL (0.19 g, 1.3 mmol) tetrafluorobenzene. The reaction mixture was stirred for 3 days at 100° C. Next it was extracted with chloroform and water. The organic phase was dried with sodium sulfate and concentrated. 1.66 g raw product was obtained as a light-yellowish solid (GCMS: 79%, M=382). The product was recrystallized from chloroform and then the mother liquor was precipitated again with methanol, yielding 620 mg of a pure white product (GCMS: 100%). From 500 mg, 230 mg sublimed (corresponding to 57% of the theoretical), melting point: 230° C.

Conductivity Measurements:

All the materials used were additionally purified by gradient sublimation.

5,12-Dioxa-7,14-dithia-pentacene was co-vaporized together with 10 mol % 2-(6-dicyanomethylene-1,3,4,5,7,8-hexafluoro-6H-naphthalen-2-ylidene)-malononitrile. The conductivity of the doped 50 nm layer measured was 1.9×10-5 S/cm. 5,12-dioxa-7,14-dithia-pentacene was vaporized already as a mixed layer together with 10 mol % 2,2',2''-(cyclopropane-1,2,3-triylidene)tris(2-(2,3,5,6-tetrafluor-4-(trifluormethyl)phenyl)-acetonitrile), so that the final layer was 50 nm thick. The conductivity measured was 3×10-7 S/cm. A doped 50-nm-thick layer of 5,9,16-trioxa-7,14,18-trithiaheptacene was co-vaporized with 10 mol % 2-(6-dicyanomethylene-1,3,4,5,7,8-hexafluor-6H-naphthalen-2-ylidene)-malononitrile. The conductivity measured was 1.1×10-3 S/cm. 3,10-Dimethoxy-5,12-dioxa-7,14-dithiapentacene was co-vaporized together with 10 mol % of the same dopant as in the preceding example (thickness 50 nm). The conductivity measured was 1.2×10-5 S/cm. Especially good properties not limited to these examples, such as power efficiency and thermal stability, were achieved with p-doping using the following p-dopants: 2,2'-(perfluoronaphthalene-2,6-diylidene)dimalononitrile; 2,2'-(2,5-dibromo-3,6-difluorcyclohexa-2,5-diene-1,4-diylidene)-dimalononitrile; 2,2',2''-(cyclopropane-1,2,3-triylidene)tris(2-(2,6-dichlor-3,5-difluoro-4-(trifluormethyl)phenyl)acetonitrile; 2,2',2''-(cyclopropane-1,2,3-triylidene)tris(2-(4-cyanoperfluorophenyl)-acetonitrile). All the measurements were performed at room temperature. The conductivity measurements were performed in vacuo in a protective gas atmosphere or in sealed samples with very little or no deviations in the measured values.

SYNTHESIS EXAMPLE 4

6,6'-bis(5,12-Dioxa-7,14-dithia-pentacene)

5.30 g 2-mercaptophenol (42.0 mmol, 5 eq.) was dissolved in 100 mL DMF under argon and added by drops to a suspension of 11.6 g potassium carbonate (84.0 mmol, 10 eq.) in 100 mL DMF. The mixture was stirred for 30 minutes and then 2.50 g 4,4-H-octafluorobiphenyl (8.5 mmol) was added. The mixture was then heated at reflux for six days (reaction control by HPLC-MS C18). On day 4, another equivalent of mercaptophenol was added. After the end of the reaction the DMF was removed under reduced pressure and the residue was dissolved in 100 mL chloroform and stirred with water, 1N sodium bicarbonate solution and again once with water (50 mL each). The organic phase was dried and concentrated. The solid residue was precipitated from chloroform and methanol and recrystallized from isopropanol.

SYNTHESIS EXAMPLE 5

N,N,N'N'-Tetraphenyl-5,12-dioxa-7,14-dithiapentacene-6,13-diamine

Step 1: Bisamination of Hexafluorobenzene

Sodium hydride (2.80 g, 118 mmol) washed with hexane was suspended in dry dimethylformamide (200 mL) under an argon atmosphere. To the suspension was added by drops a solution of diphenylamine (20.0 g, 118 mmol) in dimethylformamide (200 mL), forming hydrogen (!). The suspension was stirred for 30 minutes and then hexafluorobenzene (10.0 g, 54.0 mmol, 6.2 mL) was added through a syringe. The reaction mixture was stirred overnight at 100° C. Next the solvent was removed on a rotary evaporator. The residue was dissolved in chloroform and washed repeatedly with water. The organic phase was dried over MgSO4, filtered and concentrated. The solid residue was extracted in methanol (2×25 mL) and the product was filtered with suction as a pure white solid (GC-MS 100%). Yield: 20.9 g.

Step 2: Aromatic Substitution with 2-mercaptophenol

Potassium t-butylate (1.62 g, 14.5 mmol) was suspended in dry dimethylformamide (30 mL) under an argon atmosphere. While cooling with ice, a solution of 2-mercaptophenal (0.91 g, 7.20 mmol) in dry dimethylformamide (30 mL) was added slowly by drops. The ice bath was removed and the reaction mixture was stirred until a light-yellowish suspension had formed (approximately 30 minutes). The 1,4-bis(diphenylamine)tetrafluorobenzene was added in substance and reaction mixture was heated for 3 days at reflux (TLC control). The solvent was removed on a rotary evaporator and the residue was dissolved in chloroform and extracted repeatedly with water. The organic phase was dried over MgSO4, filtered and concentrated. The aqueous phase was mixed with calcium chloride. The crude product was precipitated from chloroform/methanol, yielding 1.28 g (67% of the theoretical) in the form of a light-yellowish solid. HPLC-MS (measured in pyridine) showed a purity of 95%; melting point 314° C.

Synthesis Pathways for Additional Compounds:

Triangular derivatives:
5,11,17-trioxa-6,12,18-trithia-trinaphthylene

This chemical compound was synthesized in two steps. Commercially available 1,3,5-tribromobenzene, which could be reacted with phenol in a reaction mediated by Cu—(I) to form the triether, may be used as the starting compound here. The same reaction was described by van Koten (G. van Koten et al., Tetrahedron Letters, 48 (2007), 7366-7370.)

In a similar aluminum trichloride-mediated reaction, sulfur can be introduced in accordance with the synthesis of simple phenoxathienes (Eric E. Boros et al., J. Heterocyclic Chem., 35, 699-706, 1998).

By using functionalized phenols in the first step, the periphery of the target compounds can be modified accordingly.

Linear derivatives: Modification of positions 6 and 13 in the parent substance of 5,12-dioxa-7,14-dithia-pentacene Based on the donor properties of the heteroatoms, positions 6 and 13 can be modified in a variety of ways in the sense of ortho-lithiation. Another type of modification was already demonstrated on the synthesis example of N,N,N',N'-tetraphenyl-5,12-dioxa-7,14-dithiapentacene-6,13-diamine.

Linear derivatives: Modification of the peripheral positions 1, 2, 3 or 4 and/or 8, 9, 10 or 11 in the parent substance of 5,12-dioxa-7,14-dithia-pentacene

Mono- or polyhalo-substituted phenols (available commercially) may he used here because they can be converted in a first step to aryl or heteroaryl derivatives by means of conventional coupling methods mediated by a transfer medium. In another step, a mercapto group can then also be introduced by ortho-metallation to the phenol function using elemental sulfur. Regioisomers may be separated here.

These functionalized mercaptophenols can be converted to the parent substance described above in similar reactions.

The features disclosed in the description and in the claims may be essential to the implementation of the invention in its various embodiments either alone or in any combination.

The invention claimed is:

1. An electronic, optoelectronic, or electroluminescent component comprising an electronically functionally active region, wherein the electronic, optoelectronic, or electroluminescent component comprises a charge transport material, light-scattering material, or blocker material, wherein the charge transport material, light-scattering material, or blocker material comprises a heterocyclic compound, wherein the heterocyclic compound has one of the following formulas A-E:

Formula A

Formula B

Formula C

Formula D

Formula A

Formula E wherein

X and Y differ from one another but are otherwise selected independently from oxygen, sulfur, selenium, or tellurium; n is 1, 2, 3, 4, 5, or 6; and $R_1$-$R_9$ are selected independently from hydrogen, alkyl, aryl, heteroaryl, anellated carbocycle, anellated heterocycle, OR', SR', or NR$_2$', wherein R' is selected independently from alkyl, aryl, heteroaryl, anellated carbocycle, or anellated heterocycle.

2. The electronic, optoelectronic, or electroluminescent component according to claim 1, wherein the charge transport material, light-scattering material, or blocker material comprises doped or undoped hole conductors, undoped exciton blockers, or undoped electron blockers.

3. A heterocyclic compound according to one of formulas A-E:

Formula A

Formula B

Formula C

Formula D

-continued

Formula E wherein X and Y differ from one another but are otherwise selected independently from oxygen, sulfur, selenium, or tellurium; n is 1, 2, 3, 4, 5, or 6; in formula A, $R_1$-$R_6$ are selected independently from alkyl, aryl, heteroaryl, anellated carbocycle, anellated heterocycle, OR', $NR_2$'' or SR''; wherein for formula B, $R_1$-$R_6$ are selected independently from alkyl, aryl, heteroaryl, anellated carbocycle, anellated heterocycle, OR', SR', or $NR_2$'; wherein for formulas C-E, $R_{1-9}$ are selected independently from hydrogen, alkyl, aryl, heteroaryl, anellated carbocycle, anellated heterocycle, OR', SR', or $NR_2$'; wherein, in each occurrence, R' is selected independently from alkyl, aryl, heteroaryl, anellated carbocycle, or anellated heterocycle, with the proviso that in formula A, R' is not alkyl; and wherein R'', in each occurrence, is selected independently from alkyl, aryl, heteroaryl, anellated carbocycle, or anellated heterocycle.

4. The heterocyclic compound according to claim 3, wherein n is 1.

5. The heterocyclic compound according to claim 3, wherein X and Y are selected from oxygen or sulfur.

6. The heterocyclic compound according to claim 3, wherein the heterocyclic compound is selected from 5,12-dioxa-7,14-dithia-pentacene, N,N,N',N'-tetraphenyl-5,12-dioxa-7,14-dithia-pentacene-6,13-diamine, 3,10-dimethoxy-5,12-dioxa-7,14-dithiapentacene, 5,9,16-trioxa-7,14,18-trithiaheptacene, 6,6'-bis(5,12-dioxa-7,14-dithia-pentacene), or 5,11,17-trioxa-6,12,18-trithia-trinaphthylene.

7. An organic semiconductor material comprising a charge transport layer, light-scattering layer, or blocking layer, wherein the charge transport layer, light-scattering layer, or blocking layer comprise(s) a heterocyclic compound according to claim 3.

8. The organic semiconductor material of claim 7, wherein the charge transport layer, light-scattering layer, or blocking layer is doped with at least one dopant.

9. An electronic, optoelectronic, or electroluminescent component comprising an electronically functionally active region, wherein the electronically active region comprises at least one heterocyclic compound of claim 3.

10. The component according to claim 9, wherein the heterocyclic compound is in crystallized form in an organic light-scattering layer.

11. The component according to claim 10, wherein the light-scattering organic layer is free of polymers.

12. The component according to claim 10, wherein the light-scattering organic layer has an optical refractive index which is greater than or equal to the optical refractive index of the light-emitting organic layer.

13. The component according to claim 10, wherein the light-scattering organic layer has an optical refractive index in the range of about 1.5 to about 2.2.

14. The component according to claim 10, wherein crystallites in the light-scattering organic layer are >500 nm in size on the average.

15. The electronic, optoelectronic, or electroluminescent component according to claim 10, wherein the electronic, optoelectronic, or electroluminescent component comprises an organic light-emitting diode, a field effect transistor, a photodetector, or an organic solar cell.

16. The component according to claim 10, wherein the light-scattering organic layer has an optical refractive index in the range of about 1.4 to about 1.8.

17. An electronic, optoelectronic, or electroluminescent component comprising an electronically functionally active region, wherein the electronic, optoelectronic, or electroluminescent component comprises at least one heterocyclic compound or mixtures of the isomers thereof in crystallized form in an organic light-scattering layer, the heterocyclic compound having a formula according to one of formulas F or G:

Formula F

Formula G wherein X and Y differ from one another but are otherwise selected independently from oxygen, sulfur, selenium, or tellurium; n is 1, 2, 3, 4, 5, and $R_1$-$R_6$ are hydrogen.

* * * * *